United States Patent
Patchen et al.

(10) Patent No.: US 7,022,685 B2
(45) Date of Patent: *Apr. 4, 2006

(54) VERY HIGH MOLECULAR WEIGHT β-GLUCANS

(75) Inventors: Myra L. Patchen, Framingham, MA (US); Spiros Jamas, Boston, MA (US); D. Davidson Easson, Jr., Shrewsbury, MA (US); Gary R. Ostroff, Worcester, MA (US)

(73) Assignee: Biopolymer Engineering, Inc., Eagan, MN (US)

( * ) Notice: Subject to any disclaimer, the term of this patent is extended or adjusted under 35 U.S.C. 154(b) by 160 days.

This patent is subject to a terminal disclaimer.

(21) Appl. No.: 10/094,686

(22) Filed: Mar. 7, 2002

(65) Prior Publication Data

US 2002/0143174 A1    Oct. 3, 2002

Related U.S. Application Data

(63) Continuation of application No. 09/325,152, filed on Jun. 3, 1999, now Pat. No. 6,369,216, which is a continuation of application No. 09/161,047, filed on Sep. 25, 1998, now abandoned.

(51) Int. Cl.
*A61K 31/715* (2006.01)
*C07H 1/00* (2006.01)
*A01N 25/00* (2006.01)

(52) U.S. Cl. .............. 514/54; 536/123.1; 536/123.12; 536/124; 514/885; 514/944; 514/951; 514/959; 514/962

(58) Field of Classification Search .......... 536/123.12, 536/123.1, 124; 514/54, 885, 944, 951, 959, 514/962
See application file for complete search history.

(56) References Cited

U.S. PATENT DOCUMENTS

| | | | |
|---|---|---|---|
| 3,943,247 A | 3/1976 | Komatsu et al. | 424/180 |
| 4,138,479 A | 2/1979 | Truscheit et al. | 424/88 |
| 4,237,266 A | 12/1980 | Sugiura et al. | 536/1 |
| 4,707,471 A | 11/1987 | Larm et al. | 514/54 |
| 4,739,046 A | 4/1988 | Di Luzio et al. | 536/117 |
| 4,761,402 A | 8/1988 | Williams et al. | 514/54 |
| 4,810,646 A | 3/1989 | Jamas et al. | 435/101 |
| 4,946,450 A | 8/1990 | Erwin | 604/294 |
| 4,975,421 A | 12/1990 | Williams et al. | 514/54 |
| 4,992,540 A | 2/1991 | Jamas et al. | 536/123 |
| 5,032,401 A | 7/1991 | Jamas et al. | 424/426 |

(Continued)

FOREIGN PATENT DOCUMENTS

EP    0322393    1/1989

(Continued)

OTHER PUBLICATIONS

Janusz, M.J., et al., "Isolation of Soluble Yeast β-Glucans that Inhibit Human Monocyte Phagocytosis Mediated by β-Glucans Receptors," *J. Immunol.*, 137:3270-3276 (1986).

(Continued)

*Primary Examiner*—James O. Wilson
*Assistant Examiner*—Everett White
(74) *Attorney, Agent, or Firm*—Hamilton, Brook, Smith & Reynolds, P.C.

(57) ABSTRACT

The invention pertains to compositions and therapeutic and prophylatic methods for treating/preventing infections in an animal or human by administering a soluble β-glucan composition comprising β-glucan molecules having an average molecular weight of at least 1,000,000 daltons, as determined by multi-angle laser light scattering (VHMW-glucan).

12 Claims, 8 Drawing Sheets

U.S. PATENT DOCUMENTS

| | | | | |
|---|---|---|---|---|
| 5,057,503 | A | 10/1991 | Czop et al. | 514/54 |
| 5,320,849 | A | 6/1994 | Hagiwara et al. | 424/442 |
| 5,322,841 | A | 6/1994 | Jamas et al. | 514/54 |
| 5,401,647 | A | 3/1995 | Tanaka et al. | 435/176 |
| 5,474,984 | A | 12/1995 | Tanaka et al. | 514/23 |
| 5,488,040 | A | 1/1996 | Jamas et al. | 514/54 |
| 5,504,079 | A | 4/1996 | Jamas et al. | 514/54 |
| 5,532,223 | A | 7/1996 | Jamas et al. | 514/54 |
| 5,622,939 | A | 4/1997 | Jamas et al. | 514/54 |
| 5,783,569 | A | 7/1998 | Jamas et al. | 514/54 |
| 5,817,643 | A | 10/1998 | Jamas et al. | 514/54 |
| 6,084,092 | A * | 7/2000 | Wakshull et al. | 536/123.12 |
| 6,369,216 | B1 * | 4/2002 | Patchen et al. | 536/123.12 |

FOREIGN PATENT DOCUMENTS

| | | |
|---|---|---|
| EP | 0 322 393 A1 | 6/1989 |
| EP | 0416343 | 3/1991 |
| EP | 0463540 | 1/1992 |
| GB | 2076418 | 12/1981 |
| JP | 55071701 | 8/1980 |
| JP | 56076401 | 9/1981 |
| JP | 59045301 | 6/1984 |
| JP | 59210901 | 4/1995 |
| WO | 91/03248 | 3/1991 |
| WO | 91/03495 | 3/1991 |
| WO | 92/13896 | 8/1992 |
| WO | 94/03498 | 2/1994 |
| WO | 94/03500 | 2/1994 |
| WO | 94/04163 | 3/1994 |

OTHER PUBLICATIONS

Manners, D.J., et al., "The Structure of a β-(-3)-D-Glucan from Yeast Cell Walls," *Biochem. J.*, 135:19-30 (1973).

Fleet, G.H., et al., "Isolation and Composition of an Alkali-Soluble Glucan from the Cell Walls of *Saccharomyces cerevisiae*," *J. Gen. Microbio.*, 94:180-192 (1976).

Miyazaki, T., et al., "Structural Examination of Antitumour, Water-Soluble Glucans from *Grifora umbellata* by Use of Four Types of Glucanases," *Carbohydrate Research*, 65:235-243 (1978).

Reiskind, J.B. and Mullins, J.T., "Molecular Architecture of the Hyphal Wall of *Achlya ambisexualis* Raper. II. Ultrastructural Analyses and a Proposed Model," *Can. J. Microbiol.*, 27:1100-1105 (1981).

Latgé, J.P., et al., "Composition Chimique et Ultrastructure des Parois des Hyphaux et des Azygospores de *Conidiobolus obscurus*," *Can. J. Microbiol.*, 30:1507-1521 (1984).

Sherwood, E.R., et al., "Soluble Glucan and Lymphokine-Activated Killer (LAK) Cells in the Therapy of Experimental Hepatic Metastases," *Chemical Abstracts*, 108:179752v (1988).

Hara, C., et al., "A Branched (1-3)-β-D-Glucan from a Water Extract of *Dictyophora indusiata* FISCH," *Carb. Res.*, 145:237-246 (1986).

Goldman, R., "Induction of a β-1,3-D-Glucan Receptor in P388D1 Cells Treated with Retinoic Acid or 1,25-dihydroxyvitamin $D_3$," *Immunology*, 63:319-324 (1988).

Konopski, A., et al., "Phagocytosis of β-1,3-D-Glucan-Derivatized Microbeads by Mouse Peritoneal Macrophages Involves Three Different Receptors," *Scand. J. Immunol.*, 33:297-306 (1991).

Williams, D.L., et al., "Development of a Water-Soluble, Sulfated (1-3)-β-D-Glucan Biological Response Modifier Derived from *Saccharomyces cerevisiae*," *Carbohydrate Research*, 235:247-257 (1992).

Williams, D.L., et al., "A Sequential Multi-Assay Protocol for the Preclinical Assessment of Natural Product Complex Carbohydrate Immunomodulators," *Develop. Biol. Standard*, 77:129-136 (1992).

Williams, D.L., et al., Development, Physiochemical Characterization and Preclinical Efficacy Evaluation of a Water Soluble Glucan Sulfate Derived from *Saccharomyces cerevisiae, Immunopharmacology*, 22:139-156 (1991).

Pretus, H.A., et al., "Isolation, Physiochemical Characterization and Preclinical Efficacy Evaluation of Soluble Scleroglucan," *J. Pharmacol. Exp. Therap.*, 257:500-510 (1991).

Bacon, J., et al., "The Glucan Components of the Cell Wall of Baker's Yeast (*Saccharomyces cerevisiae*) Considered in Relation to its Ultrastructure," *Biochem. J.*, 114:557-567 (1969).

Vestnick Federalniho Uradu Pro Vynalezy, 10:111 (1989).

Vestnick Federalniho Uradu Pro Vynalezy, 11:122-123 (1989).

Onderdonk, A.B., et al., "Anti-Infective Effect of Poly-β1-6-Glucotrisyl-β1-3-Glucopyranose Glucan In Vivo," *Infect. Immun.*, 60:1642-1647 (1992).

Abel, G. and Czop, J.K., "Activation of Human Monocyte GM-CSF and TNF-α Production by Particulate Yeast Glucan," International Congress for Infectious Diseases, Montreal Canada (Abstract) Jul. 15-19, 1990.

Chihara, G., et al., "Lentinan as a Host Defense Potentiator (HPD)," *Int. J. Immunotherapy*, 4:145-154 (1989).

Sherwood, E.R., et al., "Enhancement of Interleukin-1 and Interleukin-2 Production by Soluble Glucan," *Int. J. Immunopharm.*, 9(3):261-267 (1987).

Williams, D.L., et al., "Pre-clinical Safety Evaluation of Soluble Glucan," *Int. J. Immunopharm.*, 10(4):405-414 (1988).

Browder, W., et al., "Beneficial Effect of Enhanced Macrophage Function in the Trauma Patient," *Ann. Surg.*, p. 605-613 (1990).

Jamas, et al., "A Novel Class of Macrophage-Activating Immunomodulators," ACS Symposium Series, *Polymeric Drugs and Delivery Systems*, Chapter 5, pp. 44-51 (1991).

Shiota, M., et al., "Comparison of β-Glucan Structures in a Cell Wall Mutant of *Saccharomyces cerevisiae* and the Wild Type," *J. Biochem.* 98:1301-1307 (1985).

Jamas, et al., "PGG-A Novel Class of Macrophage Activating Immunomodulators," International Congress for Infectious Diseases, Montreal, Canada (Abstract), Jul. 15-19, 1990.

Katzen, et al., "PGG, a Glucose Polymer, Primes Interleukin-1 and Tumor Necrosis Factor Production," International Congress for Infectious Diseases, Montreal, Canada (Abstract), Jul. 15-19, 1990.

Shah, et al., "Influence of PGG on the Phagocytosis of *Staphylococcus aureus* or *Escherichia coli*," International Congress for Infectious Diseases, Montreal, Canada (Abstract), Jul. 15-19, 1990.

Onderdonk, A.B., "Effect of a New Carbohydrate Polymer on Survival in a Mouse Model for Experimental *E. coli* Sepsis," International Congress for Infectious Diseases, Montreal, Canada (Abstract), Jul. 15-19, 1990.

Arbo, A. and Santos, J.I., "Effect of PGG on Neutrophil (PMN) Function in Experimental Malnutrition," International Congress for Infectious Diseases, Montreal, Canada (Abstract), Jul. 15-19, 1990.

Onderdonk, A.B., et al., "Protective Effect of a New Carbohydrate Polymer in a Rat Model for Experimental Intraabdominal Sepsis," First International Congress on Biological Response Modifiers, Quebec, Canada, (Abstract), Mar., 1991.

Lagrange, P.H. and Fourgeaud, M., "Enhanced Natural Resistance Against Severe Disseminated *Candida albicans,*" *Int'l J. Experimental Clin. Chemotherapy*, 40(1):48-55 (1991).

Sakurai, et al., "Intravenously Administered (1-3)-β-D-Glucan, SSG, Obtained from *Sclerotinia sclerotiorum* IFO9395 Augments Murine Peritneal Macrophage Function In Vivo," *Chem. Pharm. Bull.*, 40(8):2120-2124 (1992).

Jamas, et al., "PGG-A Novel Class of Macrophage Activating Immunomodulators," *Polymer Preprints*, 31:194-195 (1990).

Sasaki, et al., "Antitumor Activity of Degraded Products of Lentinan: Its Correlation with Molecular Weight," *Gann* 67:191-195 (1976).

Di Luzio, et al., "Comparative Tumor-Inhibitory and Anti-Bacterial Activity of Soluble and Particulate Glucan," *Int. J. Cancer* 24:773-779 (1979).

Burgaleta, C. and Golde, D.W., "Effect of Glucan of Granulopoiesis and Macrophage Genesis in Mice," *Cancer Research*, 37:1739-1742 (1977).

Kenyon, A.J., "Delayed Wound Healing in Mice Associated with Viral Alteration of Macrophages," *Am. J. Vet. Res.*, 44(4):652-656 (1983).

Babineau, T., et. al., "Randomized Phase I/II Trial of a Macrophage-Specific Immunomodulator PGG-Glucan (Betafectin™) in High Risk Surgery Patients," Clinical Congress of the American College of Surgeons, San Francisco, CA, Oct. 11, 1993.

Babineau, T., et. al., "Randomized Multicenter Phase I/II Trial of a Macrophage-Specific Immunomodulator (PGG-Glucan) in High Risk Surgery Patients," Surgical Infection Society Meeting, Apr., 29, 1994.

Adachi, Y., et al., "Enhancement of Cytokine Production by Macrophages Stimulated with (1-3)-β-D-Glucan, Grifolan (GRN), Isolated from *Grifola frondosa,"* *Biol. Pharm. Bull.*, 17(12):1554-1560 (1994).

Babineau, T.J., et al., "A Phase II Multicenter, Double-blind, Randomized, Placebo-Controlled Study of Three Dosages of an Immunomodulator (PGG-Glucan) in High Risk Surgical Patients", *Archives of Surgery, 129*:1204-1210 (1994).

Babineau, T.J., et al., "Randomized Phase I/II Trial of a Macrophage-Specific Immunomodulator (PGG-Glucan) in High Risk Surgical Patients", *Annals of Surgery, 220*(5): 601-609 (1994).

Norton, J.A., "Biological Therapy of Sepsis", *Annals of Surgery, 220*(5):599-600 (1994).

Tumor Necrosis Factor: A Biological Enigma, *Science Impact*, pp. 5-6, Jun. 1989.

Dinarello, C.A. and Neta, R., "An Overview on Interleukin-1 as a Therapeutic Agent", *Biotherapy, 1*:245-254 (1989).

Van der Meer, J.W.M., et al., "Concentrations of Immunoreactive Human Tumor Necrosis Factor Alpha Produced by Human Mononuclear Cells In Vitro," *Journal of Leukocyte Biology* 43:216-223 (1988).

Dinarello, C.A., "Interleukin-1," *Reviews of Infectious Diseases*, 6(1):51-95 (1984).

Duvic, M., et al., "Glucan-Induced Keratoderma in Acquired Immunodeficiency Syndrome," *Arch. Dermatol.*, 123:751-756 (1987).

Adachi, Y., et al., "Macrophage Activation in Vitro by Chemically Cross-Linked (1-3)-β-D-Glucans," *Chem. Pharm. Bull.*, 38(4):988-992 (1990).

Sietsma, J.H. and Wessels, J.G.H., "Solubility of (1-3)-β-D-Glucan in Fungal Walls: Importance of Presumed Linkage between Glucan and Chitin", *J. Gen. Microbiology*, 125:209-212 (1981).

Mork, A. et al., "Effects of Particulate and Soluble (1-3)-β-Glucans on $Ca^{2+}$ Influx in NR8383 Alveolar Macrophages", *Immunopharmacology, 40*:77-89 (1998).

Williams, D.L. and Browder, I.W., "Development of Natural Product (1-3)-β-D-Glucan Polymers as Immune-stimulating Pharmaceuticals", *Polymers for Advanced Technologies, 5*: 529-534 (Sep. 10, 1993).

Kulicke, W. et al., "Correlation Between Immunological Activity, Molar Mass, and Molecular Structure of Different (1-3)-β-D-Glucans", *Carbohydrate Research, 297*:135-143 (1997).

Furey, S.E., "Very High Molecular Weight β-Glucan Stimulates Clearance of *E. coli* in a Murine Infection Model", A Major Qualifying Project Report submitted to the Faculty of Worcester Polytechnic Institute, (1998).

* cited by examiner

VERY HIGH MOLECULAR WEIGHT β-GLUCANS

RELATED APPLICATIONS

This application is a continuation of U.S. application Ser. No. 09/325,152, filed Jun. 3, 1999, which is a continuation of Ser. No. 09/161,047, filed Sep. 25, 1998, the entire teaching of which are incorporate herein by reference.

BACKGROUND OF THE INVENTION

Underivatized, aqueous soluble β(1,3)-glucan (also known as PGG-glucan, triple helix-glucan (TH-glucan) or Betafectin®) is a novel and unique soluble β-glucan manufactured through a proprietary process. The biological activity of this molecule is clearly distinguishable from particulate or other soluble β-glucans. Numerous laboratories have reported direct induction of arachidonic acid metabolites (Czop et al., *J. Immunol.*, 141(9):3170–3176 (1988)), cytokines (Abel and Czop, *Intl. J. Immunopharmacol.*, 14(8):1363–1373 (1992); Doita et al., *J. Leuk. Biol.*, 14(2):173–183 (1991)) and oxidative burst (Cain et al., *Complement*, 4:75–86 (1987); Gallin et al., *Int. J. Immunopharmacol.*, 14(2):173–183 (1992)) by both particulate and soluble forms of β-glucans. In contrast, underivatized, aqueous soluble β(1,3)-glucan does not directly activate leukocyte functions such as oxidative burst activity (Mackin et al., *FASEB J.*, 8:A216 (1994)), cytokine secretion (Putsiaka et al., *Blood*, 82:3695–3700 (1993)) or proliferation (Wakshull et al., *J. Cell. Biochem. suppl.*, 18A:22 (1994)). Instead, underivatized, aqueous soluble β(1,3)-glucan primes cells for activation by secondary stimuli (Mackin et al. (1994); Brunke-Reese and Mackin, *FASEB J.* 8:A488 (1994); and Wakshull et al. (1994)).

The biological activity of β-glucans is mediated through specific receptors located on target cells. Several groups of investigators have described receptors which bind to and mediate phagocytosis of particulate β-glucan preparations (e.g., zymosan-like particles; Goldman (*Immunology*, 63(2):319–324 (1988); *Exp. Cell. Res.*, 174(2):481–490 (1988); Engstad and Robertsen, *Dev. Comp. Immunol.*, 18(5):397–408 (1994); Muller et al., *Res. Immunol.*, 145:267–275 (1994)); Czop, *Advances in Immunol.*, 38:361,398 (1986)); and have partially characterized these receptors (Czop and Kay, *J. Exp. Med.*, 173:1511–1520 (1991); Szabo et al., *J. Biol. Chem.*, 270:2145–2151 (1995)). The leukocyte complement receptor 3 (CR3, also known as MAC 1 or CD11b/CD18) has been reported to bind both particulate and some soluble β-glucans, as well as other polysaccharides (Thornton et al., *J. Immunol.*, 156:1235–1246 (1996)). A soluble aminated β-glucan preparation has been shown to bind to murine peritoneal macrophages (Konopski et al., *Biochim. Biophys. Acta*, 1221:61–65 (1994)), and a phosphorylated β-glucan derivative has been reported to bind to monocyte cell lines (Muller et al., *J. Immunol.*, 156:3418–3425 (1996)).

SUMMARY OF THE INVENTION

The present invention relates to β-glucan compositions comprising β-glucan molecules having an average molecular weight of at least 1,000,000 daltons, as determined by multi-angle laser light scattering (MALLS), and referred to herein as very high molecular weight glucans (VHMW-glucans). The VHMW-glucans are soluble in aqueous solutions and are underivatized, i.e., the VHMW-glucans have not been substantially modified by substitution with functional groups. The VHMW-glucans of the invention have a high affinity for the TH-glucan receptor on human monocytes, as well as a novel receptor located primarily on rat NR8383 macrophages, particularly alveolar macrophages. The β-glucan compositions of the present invention have been shown to enhance host immune defense mechanisms to infection, but do not induce an inflammatory response. Specifically, VHMW-glucans retain a specific subset of immunological properties common to β-glucans but uniquely do not induce the production of detrimental pro-inflammatory cytokines, such as TNF-α, IL-1β and IL-6. Further, VHMW-glucans have been shown to accelerate bacterial clearance and increase platelet counts in both rat and mice infection models.

The VHMW-glucans can be formulated into a composition appropriate for parenteral (e.g., intravenous, interparenteral, subcutaneous, intramuscular), topical, oral or internasal administration to humans and animals as an anti-infective to combat infection associated with burns, surgery, chemotherapy, bone marrow disorders and other conditions in which the immune system may be compromised. The VHMW-glucan compositions of the present invention can be used in therapeutic and/or prophylatic treatment regimens of humans and animals to enhance their immune response, without stimulating the production of certain biochemical mediators (e.g., IL-1β, TNF-α and IL-6) that can cause detrimental side effects, such as fever and inflammation. The VHMW-glucan compositions can be used for therapeutic or prophylactic application, such as immunosuppression, hematopoiesis, wound healing, prevention and treatment of infectious disease, platelet production, peripheral blood precursor cell mobilization, and induction and enhancement of myelopoeisis and thrombopoeisis.

Figure 1:
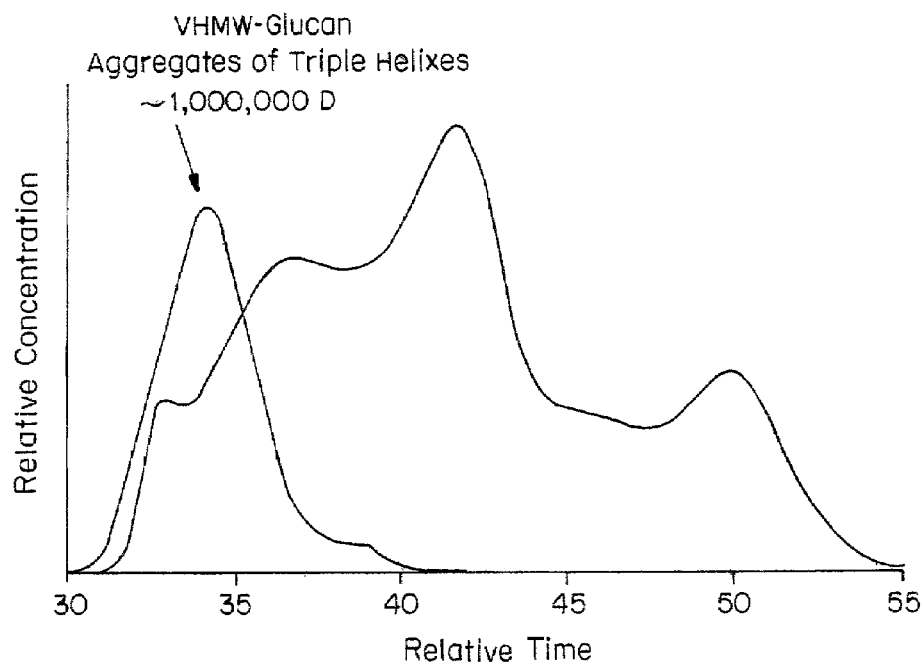
FIG. 1 is a high resolution gel permeation chromatography (HRGPC) schematic of VHMW-glucan.

The foregoing and other objects, features and advantages of the invention will be apparent from the following more particular description of preferred embodiments of the invention, as illustrated in the accompanying drawings.

DETAILED DESCRIPTION OF THE INVENTION

The present invention pertains to soluble β-glucan compositions comprising β-glucan molecules having an average molecular weight of at least 1,000,000 daltons, as determined by MALLS. In a preferred embodiment, the β-glucan molecules have an average molecular weight of from about 2,000,000 to about 4,000,000 daltons, as determined by MALLS. These β-glucan molecules are defined collectively herein as very high molecular weight-glucans (VHMW-glucans).

The VHMW-glucans of this invention are composed of a (1-3)-β-linked glucose backbone with periodic (1-6)-β-linked (1-3)-β-glucose branches and are soluble in aqueous medium under physiological conditions. A "soluble β-glucan composition", as the term is used herein, is an underivatized VHMW-glucan composition which dissolves in an aqueous medium at room temperature (about 20–25° C.) and neutral pH (from about pH 5.5 to about 7.5). An "aqueous medium", as the term is used herein, refers to water or a water-rich phase, particularly physiologically acceptable aqueous phases, including phosphate-buffered saline, saline and dextrose solutions. The term "physiological conditions", as used herein, refers to physiological pH, about pH 7, and physiological temperature, about 37° C. VHMW-glucans are not derivatized, i.e., they have not been substantially modified by substitution with functional (e.g., changed) groups or other covalent attachments. For example, they are not derivatized by phosphorylation, sulphation or amination. In a preferred embodiment, under physiological conditions the β-glucan composition consists essentially of β-glucan chains in one or more triple helix aggregate conformations.

The VHMW-glucan composition can be prepared from insoluble glucan particles (e.g., whole glucan particles), preferably derived from yeasts, according to the methods described in U.S. Pat. Nos. 5,622,939, 5,783,569 and 5,817,643. A general procedure for the preparation of insoluble yeast glucans is provided by Manners et al., *Biol. J.*, 135:19–30 (1973). Glucan particles which are particularly useful as starting materials in the present invention are whole glucan particles as described by Jamas et al. in U.S. Pat. Nos. 4,810,646, 4,992,540, 5,082,936, 5,028,703 and 5,622,939, the teachings of each of which are incorporated herein by reference in their entirety. The source of the whole glucan particles can be any fungal organism which contains β-glucans in its cell walls. Particularly useful are whole glucan particles obtained from the strains *Saccharomyces cerevisiae* R4 (NRRL Y-15903) and R4 Ad (ATCC No. 74181). Other strains of yeast which are suitable sources of whole glucan particles include *Saccharomyces delbruekii, Saccharomyces rosei, Saccharomyces microellipsodes, Saccharomyces carlsbergensis, Schizosaccharomyces pombe, Kluyveromyces lactis, Kluyveromyces fragilis, Kluyveromyces polysporus, Candida albicans, Candida cloacae, Candida tropicalis, Candida utilis, Hansenula wingei, Hansenula arni, Hansenula henricii* and *Hansenula americana*.

The VHMW-glucan portion can be separated from the starting soluble β-glucan composition using a variety of techniques. In a preferred embodiment, the very high molecular weight portion is separated from the remainder of the starting composition using gel permeation chromatography (GPC). In this embodiment, the very high molecular weight portion is separated from the starting composition by a method comprising the steps of (1) directing a β-glucan composition through a gel permeation chromatography column, and (2) collecting a high molecular weight fraction or a high molecular weight portion of a fraction of the starting composition. In one embodiment, the starting β-glucan composition is separated into two or more fractions by GPC. In this case, the faster eluting fraction is a very high molecular weight portion of the starting composition and all or a part of this fraction can be collected. In another embodiment, the starting β-glucan composition elutes as a single fraction or two or more overlapping fractions. In this case, the leading edge of the fraction or overlapping fractions can be collected.

The "leading edge" of a fraction eluting from a chromatography column is the portion of the fraction which elutes first. For example, if the fraction elutes in a given volume of eluent, the first 10 to 50% by volume of the fraction can be collected. The amount of the VHMW-glucan fraction to be collected depends upon the nature of the original β-glucan composition, for example, the distribution of molecular weights and conformations, and the chromatography conditions, such as the type of GPC column employed, the eluent and the flow rate. Optimization of these parameters is within the ordinary level of skill in the art. VHMW-glucan molecules are present in the highest molecular weight fraction and thus are expected to elute first. Therefore, if the portion collected has an aggregate number under physiological conditions which is lower than desired, the original β-glucan composition can be fractionated again, and a smaller leading edge portion can be collected to obtain a VHMW-glucan. Preferably, the parameters are optimized using an analytical scale GPC column.

The molecular weight of the VHMW-glucan fraction can be determined using a variety of methods. For example, suitable methods include light scattering techniques, such as multi-angle laser light scattering (MALLS), on-line viscometry, ultracentrifugation, osmometry, and other methods known in the art of polymer science. Preferably, the fraction should contain β-glucans having a molecular weight of at least 1,000,000 daltons, as determined by MALLS.

Figure 2:
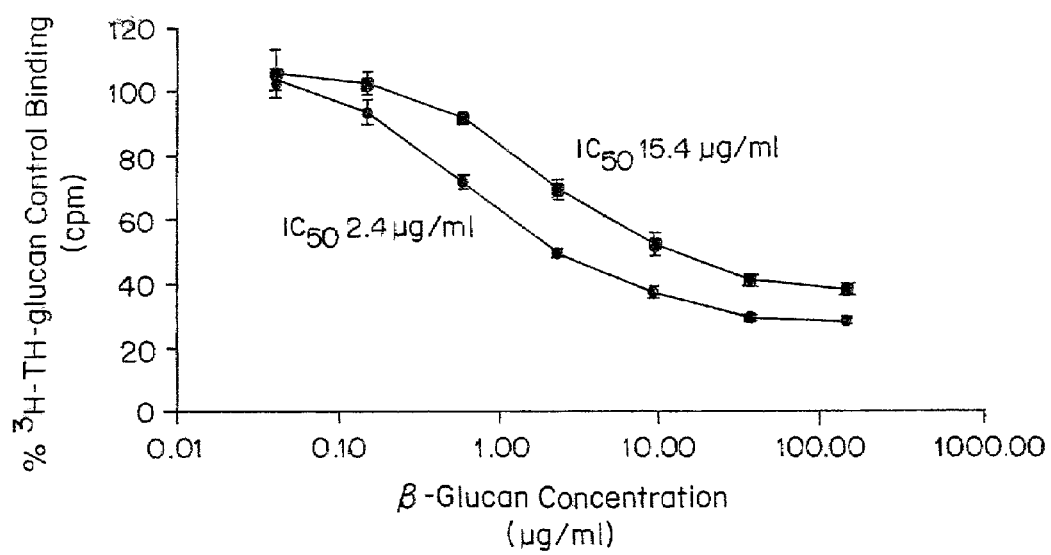
FIG. 2 is a graph illustrating competition binding data for TH-glucan (diamonds; lower curve) and VHMW-glucan (boxes; upper curve) to the glucan receptor on rat NR8383 macrophage cells.

The VHMW-glucans of this invention have a high affinity for the β-glucan receptor on human monocytes, now identified as a class of glycosphingolipids, U.S. Pat. Nos. 6,084,092 and 6,294,321. In addition, VHMW-glucan bound to the receptor on rat NR8383 alveolar macrophages and has been identified as a proteinaceous receptor, U.S. patent application Ser. No. 09/140,196, filed Aug. 26, 1998 and U.S. patent application Ser. No. 09/160,922, filed Sep. 25, 1998, as determined by competition binding assays. FIG. 2 shows the competition binding data for the TH-glucan (lower curve) and VHMW-glucans (upper curve) to the proteinaceous receptor on NR8383 cells.

Figure 4:
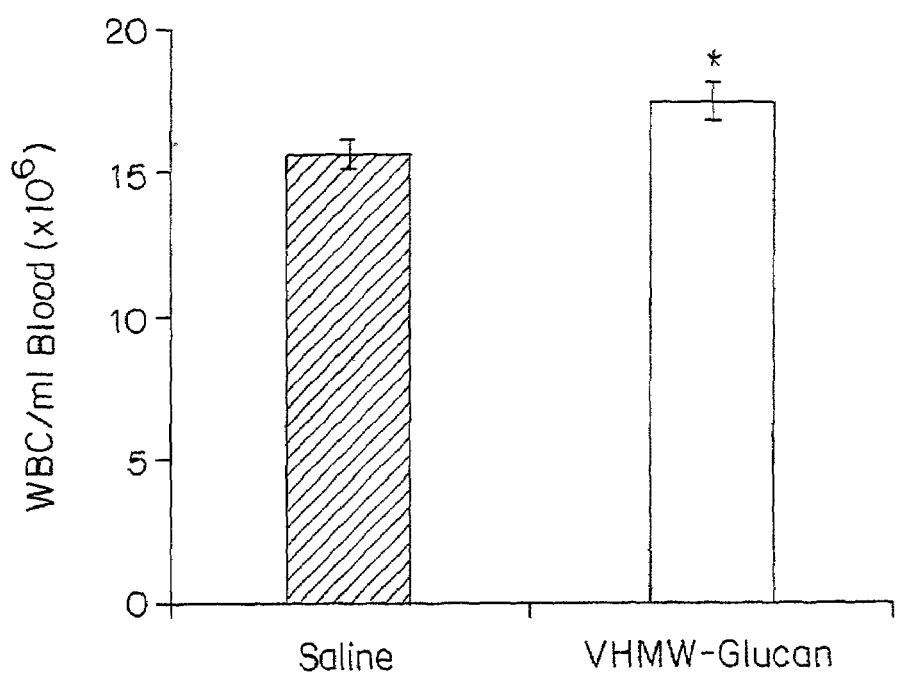
FIG. 4 is a bar graph illustrating WBC hematopoietic activity in rats challenged with *S. aureus*. Rats were intramuscularly administered either saline or VMHW-glucan at 48 hours, 24 hours and 4 hours before and 4 hours after intraperitoneal challenge with $10^8$ *S. aureus* CFU. Blood was collected from animals 48 hours after challenge.
Figure 15:
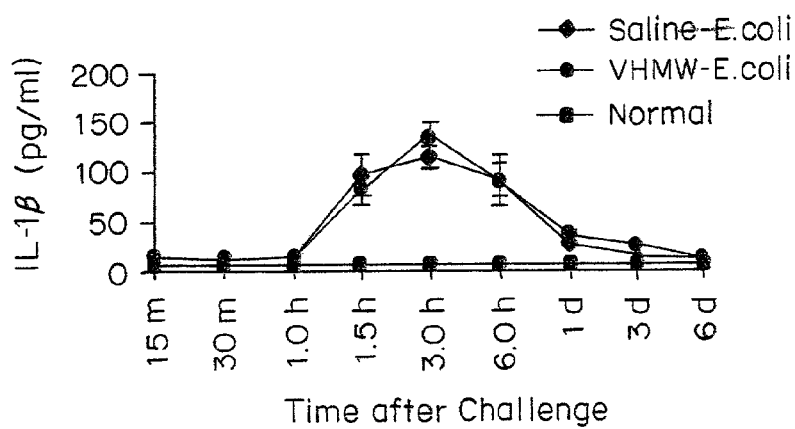
FIG. 15 is a graph illustrating the effect of VHMW-glucan therapy on serum IL-1β levels in mice challenged with *E. coli*. Saline-*E. coli* (diamond); VHMW-*E. coli* (circle); normal (box).

The VHMW-glucans have been shown to accelerate bacterial clearance and increase platelet (PLT) counts in a rat infection model with *Staphylococcus aureus* (*S. aureus*) challenge. Administration of VHMW-glucan prior to and after intraperitoneal challenge with *S. aureus*, significantly reduced blood CFU levels (1.55±0.15 compared to 2.10±0.14 log CFU/ml in controls) and slightly elevated white blood cells levels (17.78±0.67 compared to 15.60±0.50×$10^6$/ml in controls) by 48 hrs. after *S. aureus* challenge. Additionally, rats treated with VHMW-glucan also exhibited significantly (approximately 40% greater than rats treated with saline) elevated peripheral platelet counts (767±48 compared to 526±38×$10^6$/ml in controls). Based upon these data, it can be concluded that VHMW-glucan possesses myelopoietic (in vivo) and thrombopoietic (in vivo) activity, as well as being an effective anti-infective agent (FIG. 4, FIG. 15). A significant advantage of the VHMW-glucan is that it augments leukocyte microbicidal activity and induces hematopoiesis without inducing pro-inflammatory or hematopoietic cytokine production. In mice, there were no measurable amounts of serum IL-1β, IL-3, IL-6, TNF-α or GM-CSF following intravenous administration of 1 mg/kg of VHMW-glucan.

The ability of VHMW-glucan to treat *E. coli* sepsis in a murine model (sublethal infection) was also evaluated. Balb/c mice were intraperitoneally (IP) challenged with $10^8$ *E. coli* colony-forming units (CFU) and VHMW-glucan administered intramuscularly (IM) at doses ranging from 1 to 16 mg/kg at various times after bacteria challenge. Efficacy evaluations included measurement of CFU clearance from the peritoneal exudate fluid, spleen, liver, and blood on days 1, 3 and 6 after bacteria challenge. Administration of 8 mg/kg of VHMW-glucan twice daily starting 1 hour after bacteria challenge was the most efficacious dose and regimen. With this dose regimen, significantly accelerated clearance of bacteria from all tissues evaluated was observed. Reduced CFU levels correlated with significantly elevated absolute neutrophil counts. Furthermore, reduced CFU levels were correlated with elevated leukocyte oxidative burst activity. These responses occurred in the absence of any alteration of TNF-α, IL-1β and IL-6 levels in the infected mice. Single and multiple administration of VHMW-glucan after *E. coli* challenge accelerated clearance of bacteria from tissues were evaluated. However, multiple doses of VHMW-glucan are preferred to sustain CFU clearance at later days, post-challenge. The results show that VHMW-glucan can be therapeutically administered to a mammal having established infections.

The soluble β-glucan compositions of the present invention have utility as safe, effective, therapeutic and/or prophylactic agents, either alone or as adjuvants, to enhance the immune response in humans and animals. Soluble β-glucans of the invention preferably selectively activate only those components that are responsible for the initial response to infection, without stimulating or priming the immune system to release certain biochemical mediators (e.g., IL-1, TNF-α, IL-6, IL-3 and GM-CSF) that may cause adverse side effects. As such, the present soluble glucan composition can be used to prevent or treat infectious diseases in malnourished patients, patients undergoing surgery and bone marrow transplants, patients undergoing chemotherapy or radiotherapy, neutropenic patients, HIV-infected patients, trauma patients, burn patients, patients with chronic or resistant infections such as those resulting from myelodysplastic syndrome, and the elderly, all of who may have weakened immune systems. An immuno-compromised individual is generally defined as a person who exhibits an attenuated or reduced ability to mount a normal cellular or humoral defense to challenge by infectious agents, e.g., viruses, bacteria, fungi and protozoa. A protein malnourished individual is generally defined as a person who has a serum albumin level of less than about 3.2 grams per deciliter (g/dl) and/or unintentional weight loss of greater than 10% of usual body weight.

More particularly, the method of the invention can be used to therapeutically or prophylactically treat animals or humans who are at a heightened risk of infection due to imminent surgery, injury, illness, radiation or chemotherapy, or other condition which deleteriously affects the immune system. The method is useful to treat patients who have a disease or disorder which causes the normal immune response to be reduced or depressed, such as HIV infection (AIDS). For example, the method can be used to pre-initiate the immune response in patients who are undergoing chemotherapy or radiation therapy, or who are at a heightened risk for developing secondary infections or post-operative complications because of a disease, disorder or treatment resulting in a reduced ability to mobilize the body's normal responses to infection. Treatment with the soluble glucans has been shown to be particularly effective in mobilizing the host's normal immune defenses, thereby engendering a measure of protection from infection in the treated host.

The present composition is generally administered to an animal or a human in an amount sufficient to produce immune system enhancement. The mode of administration of the soluble glucan can be oral, enteral, parenteral, intravenous, subcutaneous, intraperitoneal, intramuscular, topical or intranasal. The form in which the composition will be administered (e.g., powder, tablet, capsule, solution, emulsion) will depend on the route by which it is administered. The quantity of the composition to be administered will be determined on an individual basis, and will be based at least in part on consideration of the severity of infection or injury in the patient, the patient's condition or overall health, the patient's weight and the time available before surgery, chemotherapy or other high-risk treatment. In general, a single dose will preferably contain approximately 0.01 to approximately 100 mg of glucan per kilogram of body weight, and preferably from about 0.1 to 10 mg/kg. The dosage for topical application will depend upon the particular wound to be treated, the degree of infection and severity of the wound. A typical dosage for wounds will be from about 0.001 mg/mL to about 2 mg/mL, and preferably from about 0.01 to about 0.5 mg/mL.

In general, the compositions of the present invention can be administered to an individual periodically as necessary to stimulate the individual's immune response. An individual skilled in the medical arts will be able to determine the length of time during which the composition is administered and the dosage, depending on the physical condition of the patient and the disease or disorder being treated. As stated above, the composition may also be used as a preventative treatment to pre-initiate the normal defenses which the body mobilizes against infections.

Soluble β-glucan compositions can be used for the prevention and treatment of infections caused by a broad spectrum of bacterial, fungal, viral and protozoan pathogens. The prophylactic administration of soluble β-glucan to a person undergoing surgery, either preoperatively, intraoperatively and/or post-operatively, will reduce the incidence and severity of post-operative infections in both normal and high-risk patients. For example, in patients undergoing surgical procedures that are classified as contaminated or potentially contaminated (e.g., gastrointestinal surgery, hysterectomy, cesarean section, transurethral prostatectomy) and in patients in whom infection at the operative site would present a serious risk (e.g., prosthetic arthroplasty, cardiovascular surgery), concurrent initial therapy with an appropriate antibacterial agent and the present soluble glucan preparation will reduce the incidence and severity of infectious complications.

In patients who are immunosuppressed, not only by disease (e.g., cancer, AIDS) but by courses of chemotherapy and/or radiotherapy, the prophylactic administration of the soluble β-glucan will reduce the incidence of infections caused by a broad spectrum of opportunistic pathogens including many unusual bacteria, fungi and viruses. Therapy using soluble β-glucan has demonstrated a significant radioprotective effect with its ability to enhance and prolong macrophage function and regeneration and, as a result enhance resistance to microbial invasion and infection.

In high risk patients (e.g., over age 65, diabetics, patients having cancer, malnutrition, renal disease, emphysema, dehydration, restricted mobility, etc.) hospitalization frequently is associated with a high incidence of serious nosocomial infection. Treatment with soluble β-glucan may be started empirically before catheterization, use of respirators, drainage tubes, intensive care units, prolonged hospitalizations, etc. to help prevent the infections that are commonly associated with these procedures. Concurrent therapy with antimicrobial agents and the soluble β-glucan is indicated for the treatment of chronic, severe, refractory, complex and difficult to treat infections.

The compositions administered in the method of the present invention can optionally include other components, in addition to the soluble β-glucan. The other components that can be included in a particular composition are determined primarily by the manner in which the composition is to be administered. For example, a composition to be administered orally in tablet form can include, in addition to soluble β-glucan, a filler (e.g., lactose), a binder (e.g., carboxymethyl cellulose, gum Arabic, gelatin), an adjuvant, a flavoring agent, a coloring agent and a coating material (e.g., wax or plasticizer). A composition to be administered in liquid form can include soluble β-glucan and, optionally, an emulsifying agent, a flavoring agent and/or a coloring agent. A composition for parenteral administration can be mixed, dissolved or emulsified in water, sterile saline, PBS, dextrose or other biologically acceptable carrier. A composition for topical administration can be formulated into a gel, ointment, lotion, cream or other form in which the composition is capable of coating the site to be treated, e.g., wound site.

The soluble glucan composition of the invention can also be administered topically to a wound site to stimulate and enhance wound healing and repair. Wounds due to ulcers, acne, viral infections, fungal infections or periodontal disease, among others, can be treated according to the methods of this invention to accelerate the healing process. Alternatively, the soluble β-glucan can be injected into the wound or afflicted area. In addition to wound repair, the composition can be used to treat infection associated therewith or the causative agents that result in the wound. A composition for topical administration can be formulated into a gel, ointment, lotion, cream or other form in which the composition is capable of coating the site to be treated, e.g., wound site. The dosage for topical application will depend upon the particular wound to be treated, the degree of infection and severity of the wound. A typical dosage for wounds will be from about 0.01 mg/mL to about 2 mg/mL, and preferably from about 0.01 to about 0.5 mg/mL.

Another particular use of the compositions of this invention is for the treatment of myelodysplastic syndrome (MDS). MDS, frequently referred to as preleukemia syndrome, is a group of clonal hematopoietic stem cell disorders characterized by abnormal bone marrow differentiation and maturation leading to peripheral cytopenia with high probability of eventual leukemic conversion. Recurrent infection, hemorrhaging and terminal infection resulting in death typically accompany MDS. Thus, in order to reduce the severity of the disease and the frequency of infection, compositions comprising modified glucan can be chronically administered to a patient diagnosed as having MDS according to the methods of this invention, in order to specifically increase the infection fighting activity of the patient's white blood cells. Other bone marrow disorders, such as aplastic anemia (a condition of quantitatively reduced and defective hematopoiesis) can be treated to reduce infection and hemorrhage that are associated with this disease state.

The soluble β-glucan compositions of the present invention enhance the non-specific defenses of mammalian mononuclear cells and significantly increases their ability to respond to an infectious challenge. The unique property of soluble glucan macrophage activation is that it does not result in increased body temperatures (i.e., fever) as has been reported with many non-specific stimulants of those defenses. This critical advantage of soluble glucan may lie in the natural profile of responses it mediates in white blood cells.

The soluble β-glucan compositions of the invention are also of use in methods of inducing or enhancing mobilization of peripheral blood precursor cells, elevating circulating levels of peripheral blood precursor cells and enhancing or facilitating hematopoietic reconstitution or engraftment in mammals, including humans. Peripheral blood precursor cells include stem cells and early progenitor cells which, although more differentiated than stem cells, have a greater potential for proliferation than stem cells. These methods comprise administering to the mammal an effective amount of a β-glucan composition of the present invention. Such methods are of use, for example, in the treatment of patients undergoing cytoreductive therapy, such as chemotherapy or radiation therapy.

In addition, it has been demonstrated herein that the VHMW-glucan preparation of the present invention possesses an unexpected platelet stimulating property. This property can be exploited in a therapeutic regimen for use as an adjuvant in parallel with radiation or chemotherapy treatment. Radiation and chemotherapy are known to result in neutropenia (reduced polymorphonuclear (PMN) leukocyte cell count) and thrombocytopenia (reduced platelet count). At present, these conditions are treated by the administration of colony-stimulating factors such as GM-CFS and granulocyte colony-stimulating factor (G-CSF). Such factors are effective in overcoming neutropenia, but fail to impact upon thrombocytopenia. Thus, the platelet stimulating property of the VHMW-glucan preparation of this invention can be used, for example, as a therapeutic agent to prevent or minimize the development of thrombocytopenia which limits the dose of the radiation or chemotherapeutic agent which is used to treat cancer.

The invention is further illustrated by the following Examples which are not intended to be limiting in any way. All references cited herein are incorporated in their entirety.

EXAMPLES

Example 1

Prophylatic Administration of VHMW-Glucan in Rat Infection Model

A. Materials and Methods

β-Glucans

VHMW-glucan (lot PB3-00171; MW~1,000,000 D) and triple helix-glucan (TH-glucan; lot VB4-0003; MW~150,000 D) were produced by extraction of whole glucan particles from *S. cerevisiae*, as described in U.S. Pat. No. 5,622,939. Molecular weight determinations were performed by multi-angle laser light scattering (MALLS). The physiochemical characteristics of these VHMW-glucan are illustrated in FIG. 1. The endotoxin level in both glucan preparations was less than 0.06 EU/mg based on the Limulus amebocyte lysate (LAL) assay.

Competition Studies

Cells of the NR8383 rat alveolar macrophage cell line are known to be capable of strongly responding to TH-glucan (Michalek, M. et al., *J. Leukoc. Biol.* 64:337–344, (1998); Wakshull, E. et al., *J. Leukoc. Biol.*, 1:10 (1998)). In these cells, competition for $^3$H-TH-glucan binding was used to assess VHMW-glucan binding to the glucan receptor on NR8383 cells. NR8383 cells were grown in Ham's F-12 medium (Life Technologies, Grand Island, N.Y.) containing 15% fetal bovine serum (FBS; Sigma, St. Louis, Mo.) (F-12/FBS) using standard tissue culture techniques. Cells were harvested at a cell density of approximately $3 \times 10^5$ cells/ml by scraping and centrifuging at 400×g for 5 min. at room temperature. Cells were resuspended to $3 \times 10^6$ cells/ml in phosphate buffered saline (PBS; Life Technologies, Grand Island, N.Y.) and combined with $^3$H-TH-glucan (1 μg/ml final) and either saline or various concentrations of TH-glucan or VHMW-glucan competitor. The binding reaction was allowed to proceed for 1 hr at 37° C. At the end of the incubation period, cells were washed twice with PBS by centrifugation, solubilized with 0.1 N NaOH, and radioactivity quantitated by liquid scintillation chromatography. To prepare $^3$H-TH-glucan, TH-glucan was incubated with NaIO$_4$ (10 mg/ml; Sigma, St. Louis, Mo.) in sterile pyrogen-free (SPF) water for 72 hr at room temperature. The periodate was quenched by the addition of 0.5 ml ethylene glycol. The oxidized THT-glucan was dialyzed against SPF water, and then reductively labeled with 100 mCi of NaB$^3$H$_4$ (New England Nuclear, Boston, Mass.). $^3$H-TH-glucan was separated from tritiated low molecular weight degradation products by dialysis and ultrafiltration. Purity of the labeled product was assessed by gel permeation chromatography.

Signal Transduction Studies

The in vitro biological responsiveness of NR8383 cells to VHMW-glucan was evaluated based on activation of a unique p65/p48 κB-like nuclear transcription factor (NF-κB). NF-κB was assayed using electrophoretic mobility shift assays (EMSA). Adams, D. S., et al., *J. Leukoc. Biol.* 62:865–873 (1997); Wakshull, E. et al., *J. Leukoc. Biol.* Supplement 1:10 (1998). NR8383 cells were incubated 1 hr at 37° C. in F-12/FBS containing VHMW-glucan (3 μg/ml). Following incubation, nuclear extracts were prepared from the cells as described previously (Adams, D. S., et al., *J. Leukoc. Biol.* 62:865–873 (1997); Wakshull, E. et al., *J. Leukoc. Biol.* Supplement 1:10 (1998)). All buffers were freshly supplemented with dithiothreitol (DTT; 0.5 mM), protease inhibitor cocktail, and phosphatase inhibitor cocktail. Protein concentrations were determined by Bradford assay (Pierce Chemical Co., Rockford, Ill.) against a bovine serum albumin (BSA) standard. The NF-κB consensus synthetic duplex probe used for EMSAs was previously described in Adams, D. S., et al., *J. Leuko. Biol.*, 62:865–873 (1997). $^{32}$P-labeled duplex probe was prepared with polynucleotide kinase. Labeled probe (0.5 pmol) was mixed with 3 μg of nuclear extract protein in a solution containing 10 mM Tris-HCl (pH 7.5), 50 mM NaCl, 1 m M EDTA, 1 mM DTT, 5% glycerol, 0.02% β-mercaptoethananol, 0.1–1.0 μg of poly(dI/dC) (Pharmacia, Piscataway, N.J.). Reactions were incubated at 25° C. for 20 min. Then electrophoresed under non-denaturing conditions through 4% polyacrylamide gels in 0.5×TBE buffer. Bands were visualized by autoradiography.

Animals, Drug Administration and Bacterial Challenge for in vivo Anti-Infective and Hemotopoietic Studies Virus-antibody free male Wistar rats were purchased from Charles River Breeding Laboratories (Wilmington, Mass.). Animals were housed according to the National Institutes of Health guidelines, provided food and water ad libitum, and quarantined for 7 days prior to being entered into experiments. Body weights of rats ranged from 160 g to 210 g at the time of experimentation. Saline or VHMW-glucan (1 mg/kg) was administered intramuscularly (IM) using a 25 gauge needle at 48 hr, 24 hr and 4 hr before and at 4 hr after challenge with $10^8$ colony-forming units (CFU) of a multiple antibiotic resistant clinical isolate of *S. aureus*. Stock bacteria were expanded in Nutrient Broth (NB; Difco Laboratories, Detroit, Mich.) for 8 hr at 37° C. and aliquots containing 20% sterile glycerol frozen at −80° C. until used. To determine the viability of the aliquoted bacteria, a frozen sample was thawed, serially diluted, plated onto Nutrient Agar (NA; Difco Laboratories, Detroit, Mich.), and bacterial colonies counted after a 24 hr incubation at 37° C. To prepare the bacterial inoculum, an aliquot of bacteria was thawed and diluted to the desired number of CFU/ml in PBS (Gibco Life Technologies, Grand Island, N.Y.) containing 1% dextran sulfate and a final concentration of 5% barium sulfate (wt/vol). A 0.5 ml aliquot of appropriately diluted bacteria was aseptically placed into 2 cm long×0.5 cm diameter gelatin capsules (Eli-Lilly Inc., Indianapolis, Ind.) and the capsules were implanted into the peritoneal cavity of rats. To implant the capsules, rats were anesthetized by IM injection of a mixed anesthetic cocktail consisting of Ketamine (Fort Dodge Laboratories Inc., Fort Dodge, Iowa), PromAce (Ayerst Laboratories Inc., Rouses Point, N.Y.), Xylazine (Phoenix Scientific Inc., St. Joseph, Mo.) and saline (750 mg, 10 mg, 100 mg, saline to 20 ml) using a 25 gauge needle. The anesthesia was adjusted for each rat based on body weight by administering 0.0019 ml/g body weight. After administering the anesthesia, the abdomen of each rat was shaved, cleaned with iodine solution, and a 1.5 cm anterior midline incision was made through the abdominal wall and the peritoneum. The gelatin capsule containing $10^8$ S. aureus CFU was immediately placed into the peritoneal cavity and the incision was closed with interrupted 3-D silk sutures. The total duration of surgery was less than 2 min.

Blood Sampling and Analysis

Animals were anesthetized with $O_2$: $CO_2$ (1:1) and 2 ml of blood was obtained by cardiac puncture using a 3 ml syringe with 20 gauge needle. Immediately after blood was collected, approximately 1.5 ml was expelled into a 1.7 ml Eppendorf centrifuge tube containing 5 units of heparin (Elkins-Sinn Inc., Cherry Hill, N.J.). Each animal was then humanely euthanized with $CO_2$. To obtain accurately quantifiable blood CFU levels, two concentrations of blood from each animal, 1:10 diluted and undiluted, were cultured. Twenty ml of 50° C. Tryptic Soy Agar (Becton Dickinson Microbiology Systems, Cockeysville, Md.) was plated into a sterile petri plate and a 0.5 ml aliquot of blood immediately added to the plate and thoroughly mixed into the agar by swirling the plate. Once the agar solidified, plates were incubated at 37° C. for 48 hr, then colonies counted. Blood CFU data are expressed as log CFU/ml of blood. The remaining blood from each sample was used for blood cell counts. Total white blood cell (WBC), red blood cell (RBC), and platelet (PLT) counts were performed on a System 9010+ Hematology Analyzer (Biochem Immunosystems Inc., Allentown, Pa.).

In vivo Cytokine-Induction Studies

Cytokine induction in vivo was evaluated in seven week old, female, Balb/c mice purchased from Taconic Farms (Germantown, N.Y.). Mice were barrier reared and reported by the supplier to be free of adventitious viruses and pathogenic organisms. Animals were housed ten per group in plastic Micro-Barrier cages (Allentown Caging Equipment, Allentown, N.J.) on hardwood-chip contact bedding and were provided food and chlorinated water ad libitum. Mice were allowed to acclimate to the environment of the animal facility for one week prior to being entered into experimental protocols. Mice were intravenously (IV) administered saline, 500 μg/kg E. coli lipopolysaccharide (LPS, Calbiochem, LaJolla, Calif. serotype 0127:B8) or 1 mg/kg of VHMW-glucan. At 0.5, 1.5, 3, 6, and 24 hr after drug administration, ten mice in each treatment group were anesthetized with isoflurane (AErrane®; Ohmeda PPD, Liberty Corner, N.J.) and blood collected by cardiac puncture and pooled. Serum was separated from the blood and assayed for interleukin-1β (IL-1β), interleukin-3 (IL-3), interleukin-6 (IL-6), tumor necrosis factor-α (TNF-α) and granulocyte-macrophage colony-stimulating factor (GM-CSF) by ELISA using commercial kits specific for the detection of these murine proteins (R&D Systems, Minneapolis, Minn.).

Statistical Analysis

Unless stated otherwise, results are expressed as the mean±standard error of the mean (SEM) of data obtained from replicate experiments. Unpaired t-tests were performed using Instat software (GraphPad, San Diego, Calif.) and differences were considered significant at p<0.05.

B. Results

Competition Binding Studies

Initial experiments evaluated the ability of VHMW-glucan to compete for $^3$H-TH-glucan binding on NR8383 cells (FIG. 2). From the binding competition curves, it was calculated that the glucan concentration inhibiting 50% of $^3$H-TH-glucan binding ($IC^{50}$) was 15.4 μg/ml for VHMW glucan and 2.4 μg/ml for TH-glucan. Further studies evaluated whether signal transduction events were induced by VHMW-glucan. As with TH-glucan, a unique p65/p48 NF-κB-like factor was shown to be activated by VHMW-glucan (data not shown).

VHMW-Glucan Induces In Vivo Anti-Infective Activity

Figure 3:
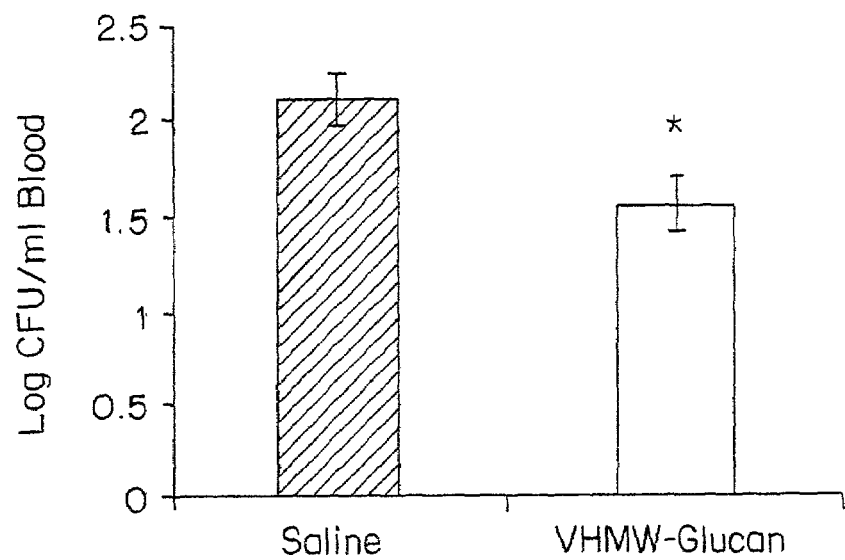
FIG. 3 is a bar graph illustrating the anti-infective activity of VHMW-glucan intramuscularly administered to rats at 48 hours, 24 hours, 4 hours before and 4 hours after intraperitoneal challenge with $10^8$ *S. aureus* CFU. Blood was collected from animals 48 hours after challenge and cultured for CFU content.

Additional studies evaluated the anti-infective potential of VHMW-glucan in rats challenged with S. aureus. Administration of VHMW-glucan to rats challenged with S. aureus resulted in significantly reduced blood CFU levels at 48 hr after challenge (FIG. 3). The literature has demonstrated that cytokine induction has been associated with anti-infective activity. To elevuate whether, VHMW-glucan induces cytokines, normal mice were treated with VHMW-glucan and the serum collected for cytokine analysis. Mice injected with LPS were used as positive controls. The data in Table 1 demonstrate that, in contrast to the IL-1β and TNF-α cytokine responses in LPS-treated mice, VHMW-glucan treatment did not induce these pro-inflammatory cytokines.

TABLE 1

Pro-Inflammatory Cytokine Production In Vivo[1]

| Time | IL-1β (LOD 7.8 pg/ml)[2] | | | TNF-α (LOD 23.4 pg/ml)[2] | | |
|---|---|---|---|---|---|---|
| (hr) | Sal | VHMW | LPS | Sal | VHMW | LPS |
| 0.5 | <7.8 | 12 | <7.8 | <23.4 | <23.4 | 1253 |
| 1.5 | <7.8 | 13 | 88 | <23.4 | <23.4 | 5688 |
| 3.0 | <7.8 | <7.8 | 86 | <23.4 | <23.4 | 291 |
| 6.0 | <7.8 | 9 | 46 | <23.4 | <23.4 | 56 |
| 24.0 | 12 | 8 | 8 | <23.4 | <23.4 | <23.4 |

[1]Balb/c mice were injected IV with either saline (Sal), VHMW-glucan (VHMW; 1 mg/kg) or LPS (500 μg/kg) and blood drawn for serum cytokine analysis by ELISA as described in the Methods and Materials. Data represent the mean of duplicate determinations.
[2]LOD = lowest limit of detection in specific ELISA assays.

VHMW-glucan Induces Hematopoietic Effects

Figure 5:
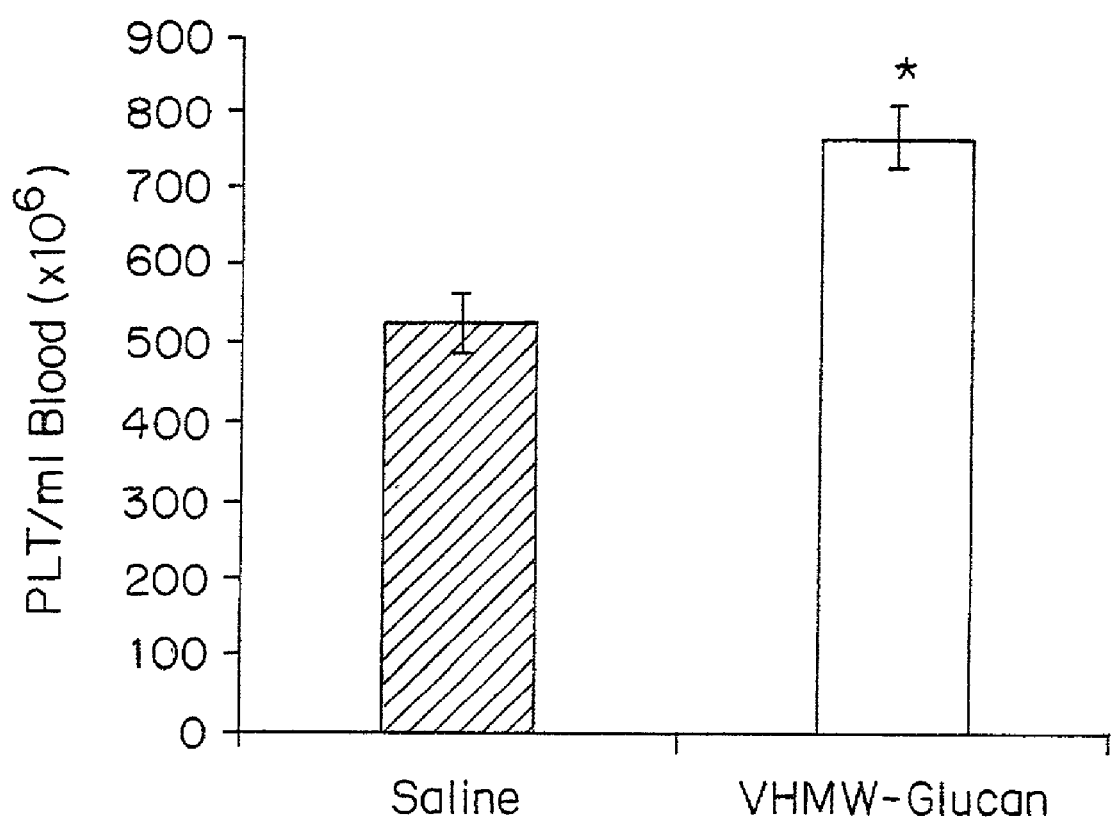
FIG. 5 is a bar graph illustrating platelet (PLT) hematopoietic activity in rats challenged with *S. aureus*. Rats were intramuscularly administered either saline or VHMW-glucan at 48 hours, 24 hours, 4 hours before and 4 hours after intraperitoneal challenge with $10^8$ *S. aureus* CFU. Blood was collected from animals 48 hours after challenge and cultured for CFU content.

In evaluating the hematopoietic effects of VHMW-glucan in rats challenged with S. aureus, elevated WBC counts were observed (FIG. 4). Rats treated with VHMW-glucan also exhibited significantly elevated PLT counts (FIG. 5). PLT counts in rats treated with VHMW-glucan were approximately 40% greater than rats treated with saline. Based on this unique PLT effect, studies were performed to evaluate whether VHMW-glucan may induce cytokines known to influence PLT production at various stages within the hematopoietic hierarchy. In these studies, the serum samples obtained from normal mice administered VHMW-glucan were assayed for IL-3 (multi-CSF), IL-6, and GM-CSF. The data presented in Table 2 illustrates that VHMW-glucan did not induce any of these hematopoietic factors.

TABLE 2

Hematopoietic Cytokine Production In Vivo[1]

| Time | GM-CSF (LOD 7.8 pg/ml)[2] | | | IL-3 (LOD 7.8 pg/ml)[2] | | | IL-6 (LOD 15.6 pg/ml)[2] | | |
|---|---|---|---|---|---|---|---|---|---|
| (hr) | Sal | VHMW | LPS | Sal | VHMW | LPS | Sal | VHMW | LPS |
| 0.5 | <7.8 | <7.8 | <7.8 | <7.8 | <7.8 | <7.8 | <15.6 | <15.6 | 590 |
| 1.5 | <7.8 | <7.8 | 69 | <7.8 | <7.8 | <7.8 | <15.6 | 21 | 33241 |
| 3.0 | <7.8 | <7.8 | 37 | <7.8 | <7.8 | <7.8 | 36 | <15.6 | 15246 |
| 6.0 | <7.8 | <7.8 | <7.8 | <7.8 | <7.8 | <7.8 | 19 | 21 | 362 |
| 24.0 | <7.8 | <7.8 | <7.8 | 19 | <7.8 | <7.8 | 35 | <15.6 | <15.6 |

[1]Balb/c mice were injected IV with either saline (Sal), VHMW-glucan (VHMW; 1 mg/kg), or LPS (500 µg/kg) and blood drawn for serum cytokine analysis by ELISA as described in the Methods and Materials. Data represent the mean of duplicate determinations.
[2]LOD = lowest limit of detection in specific ELISA assays Example 2

Therapeutic Administration of VHMW-Glucan to Enhance Bacteria Clearance in a Murine *E. coli* Sepsis Model A. Materials and Methods Animals Virus- and antibody-free, female, Balb/c mice were purchased from Taconic Farms (Germantown, N.Y.). Upon arrival, mice were housed in polycarbonate Micro-Barrier cages (Allentown Caging Equipment, Allentown, Pa.) on hardwood bedding (Sani-Chip, P. J. Murphy Forest Products Corp., Montville, N.J.), with no more than ten animals per cage. Mice were provided roduct chow (RHM 3000 Laboratory Rodent Chow, Prolab Animals Diets, Agway, Inc., Syracuse, N.Y.) and chlorinated tap water ad libitum. After arrival, mice were quarantined for 7 days prior to being entered into experiments. The average body weight of mice at the time of experimentation was 18 g.

Drug Administration.

VHMW-glucan (lot PB3-0017) was produced according to methods described in U.S. Pat. No. 5,622,939. The endotoxin level in this glucan preparation was less than 0.06 EU/mg based on the Limulus amebocyte lysate assay. VHMW-glucan was administered intramuscularly (IM) in a 0.25 ml volume at doses of 1 mg/kg, 2 mg/kg, 4 mg/kg, 8 mg/kg or 16 mg/kg. VHMW-glucan was diluted to the desired concentrations using endotoxin-free Phosphate Buffered Saline (PBS, Gibco Life Technologies, Grand Island, N.Y.). Both single and multiple treatment regimens were evaluated.

Bacteria.

A methicillin-resistant *E. coli*, originally isolated from a clinical wound site, was kindly provided by Dr. Andrew B. Onderdonk (Channing Laboratory, Harvard Medical School, Boston, Mass.) (Onderdonk, et al., *Infect. Immun.*, 60:1642–1647 (1992)). A frozen aliquot of stock bacteria was expanced in LB Broth (Sigma, St. Louis, Mo.) with shaking for 7 hr at 37° C. In preliminary growth kinetic studies, these conditions were determined to consistently produce bacteria in late log-phase. To make the working *E. coli* stock, sterile glycerol was added to the bacteria to a final concentration of 20%. Three ml of *E. coli* were then aliquoted into sterile 5 ml cryovials, snap-frozen with liquid nitrogen, and stored at −80° C. until use. Prior to use in experiments, the colony-forming unit (CFU) concentration of the bacteria was determined by thawing 4–6 cryovials of bacteria, plating on LB agar, and scoring colonies after incubation at 37° C. for 24 hours. To prepare bacterial inoculum for in vivo studies, stock cultures were diluted to the desired number of CFU/ml in PBS and administered to the mice intraperitoneally (IP) in a 0.5 ml volume.

Collection of Blood, Peritoneal Exudate Fluid and Tissues.

Mice were anesthetized with AErrane (Isoflurane® USP; Ohmeda Caribe, Inc., Puerto Rico) and peritoneal exudate fluid (PEF) collected by injecting mice IP with 5 ml Hank's buffered saline (HBSS), gently massaging the abdomen, and then withdrawing the fluid. After collecting the PEF, blood was collected from the anesthetized animals by cardiac puncture. For cell counts and plating, the blood was immediately expelled into a 1.7 ml micro-centrifuge tube (Corning Costar Corporation, Cambridge, Mass.) containing 5 units of heparin (Elkins-Sinn, Inc., Cherry Hill, N.J.). Total white blood cell (WBC), red blood cell (RBC), and platelet (PLT) counts were performed on a System 9010+ Hematology Analyzer (Biochem Immunosystems, Inc., Allentown, Pa.). For WBC differential analysis, smears of each blood sample were prepared and stained with Diff-Quik (Dade Diagnostics, Inc., Aguada, PR). The percentages of neutrophils, monocytes and lymphocytes were used to calculate absolute neutrophil counts, absolute monocyte counts, and absolute lymphocyte counts. For cytokine analysis, blood was expelled into non-hepain containing tubes, allowed to clot and centrifuged at 2500 rpm for 20 min. at 25° C. Sera were then collected, aliquoted and frozen at −80° C. until use. After PEF and blood collection animals were euthanized by cervical dislocation, and the liver and spleen were removed, placed in sterile saline on ice until homogenized to plate for CFU content. Prior to homogenizing, the weight of each tissue was recorded. Each tissue was then placed in 2 ml of sterile saline in the base unit of a sterile glass homogenizer, the sterile glass homogenizing pestal inserted and attached to the homogenizer drive unit (Bellco Biotechnology, Vineland, N.J.), and the drive until turned on for approximately 60 sec. For cell function studies, rather than homogenizing, spleen/tissue cell suspensions were prepared by pressing spleens/tissues through a stainless steel mesh screen and washing cells from the screen with 6 ml of HBSS. PEF and spleen/tissue cell counts were performed on a Counter Counter (Coulter Electronics, Inc., Hialeah, Fla.). The specific cell content of samples was assessed in cytospin preparations stained with Diff-Quik.

Plating Blood, Peritoneal Exudate Fluid and Tissue Homogenates for CFU Content.

A 50 µl aliquot of each fluid or tissue homogenate was plated on LB agar plates undiluted, and at 1:10, 1:100, and 1:1000 dilutions. Plates were then incubated at 37° C. for 24 hours and colonies scored. The log CFU/ml blood or PEF or log CFU/g of tissue was then calculated for each sample.

Oxidative Burst Assay

For oxidative burst assays, 50 µl of $1 \times 10^8$/ml of PEF and spleen cells were suspended in HBSS containing 50 µl Lucigenin (0.05 mM) (Sigma Chemical Co., St. Louis, Mo.). 100 µl of the suspension was placed into triplicate wells of 96-well plates. The plates were covered and incubated at 37° C. for 10 minutes. The cell suspension was then challenged with either Phorbol 12-myristate-13-acetate (PMA; Sigma Chemical Co., St. Louis, Mo.) at a final concentration of $10^{-6}$ M or 100 µl of a 5 mg/ml solution of opsonized Zymosan A (Sigma Chemical)(opsonized according to Methods of Hasegawa, H., et al., *J. Immun. Methods*, 210:1–10 (1997) and immediately placed in a 37° C. Microtiter Place Luminometer (Dynatech Laboratories, Chantilly, Va.) and read for 80 cycles with a 15 sec pause between cycles (approximately 90 min. total time). Data for oxidative burst activities are expressed as the area under the chmiluminescence intensity curves calculated by the luminometer software (Dynatech Laboratories, Chantilly, Va.).

Cytokine Analysis

Serum samples for cytokine analysis were collected at the specified times after VHMW-glucan treatment and cytokine levels quantitated by ELISA using commercial kits for detection of murine TNF-α, IL-1β and IL-6 (R&D Systems, Minneapolis, Minn.). To obtain positive control sera, mice were intravenously (IV) administered lipopolysaccharide (LPS; *E. coli* 0127:B8: Sigma Chemical Co., St. Louis, Mo.) at a dose of 500 µg/kg and serum samples collected at the same times as following VHMW-glucan administration.

B. Results

Establishing the *E. coli* Infection Model.

Prior to initiating VHMW-glucan studies, preliminary studies determined the maximum *E. coli* challenge that could be administered to Balb/c mice without inducing lethality. Groups of 10 mice were injected IP with $1 \times 10^5$, $1 \times 10^6$, $1 \times 10^7$, $1 \times 10^8$ or $1 \times 10^9$ *E. coli* CFU/mouse and survival monitored over a six day period. From these studies it was determined that $1 \times 10^8$ CFU/mouse was the highest nonlethal *E. coli* challenge dose. Preliminary studies also evaluated CFU clearance in mice challenged with this *E. coli* dose. These experiments demonstrated that, following challenge with $1 \times 10^8$ *E. coli*, CFU could be detected in spleen, blood, liver and peritoneal exudate fluid through day 6 after challenge.

Effects of Single Dose VHMW-glucan Therapy in Mice Infected with *E. coli*.

Figure 6:
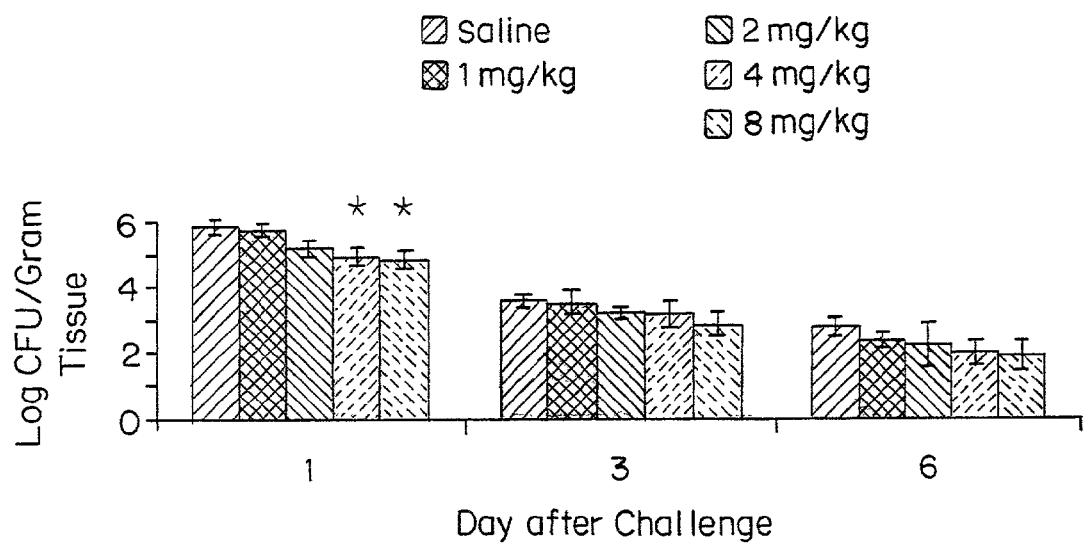
FIG. 6 is a bar graph illustrating the effect of VHMW-glucan on spleen CFU levels in mice challenged with *E. coli*. VHMW-glucan was administered as a single dose one hour after challenge.

Initial studies focused on evaluating the anti-infective effects of various VHMW-glucan doses administered IM 1 hr after *E. coli* challenge. Changes in splenic CFU levels were used as an indicator of efficacy in these initial studies. As can be seen in FIG. 6, on day 1 after challenge, VHMW-glucan induced a dose dependent reduction in splenic CFU levels which was significant at 4 mg/kg and 8 mg/kg. Significant CFU reductions, however, were no longer evident by day 3 or day 6 after VHMW-glucan administration. Overall, the optimal VHMW-glucan dose appeared to be 8 mg/kg. In a subsequent experiment, the VBMW-glucan dose was increased to 16 mg/kg, however, effects were less than observed with the 8 mg/kg dose (data not shown) and subsequent studies were thus pursued with the 8 mg/kg dose.

Effects of Multiple Dose VHMW-glucan Therapy in Mice Infected with *E. coli*.

Figure 7:
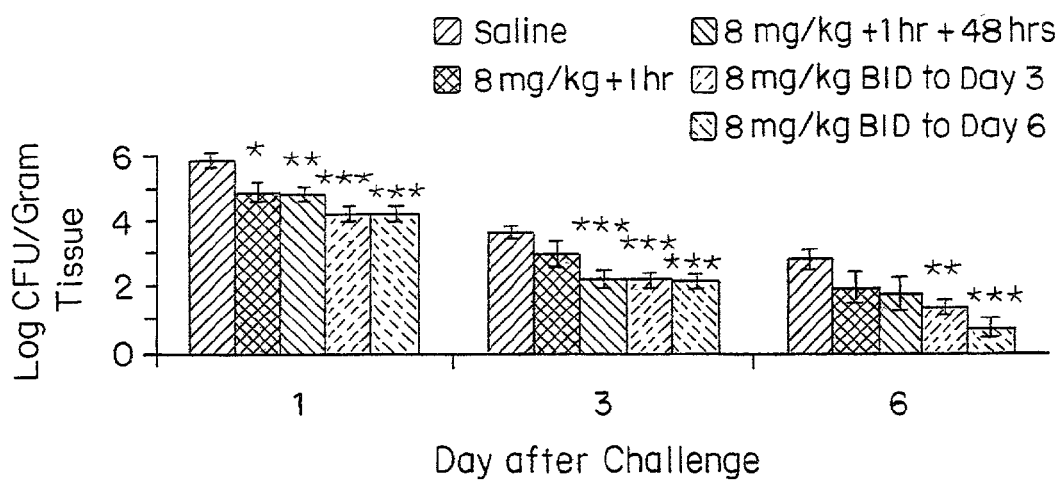
FIG. 7 is a bar graph illustrating the effect of different VHMW-glucan treatments on spleen CFU levels in mice challenged with *E. coli* (multiple dosages).
Figure 8:
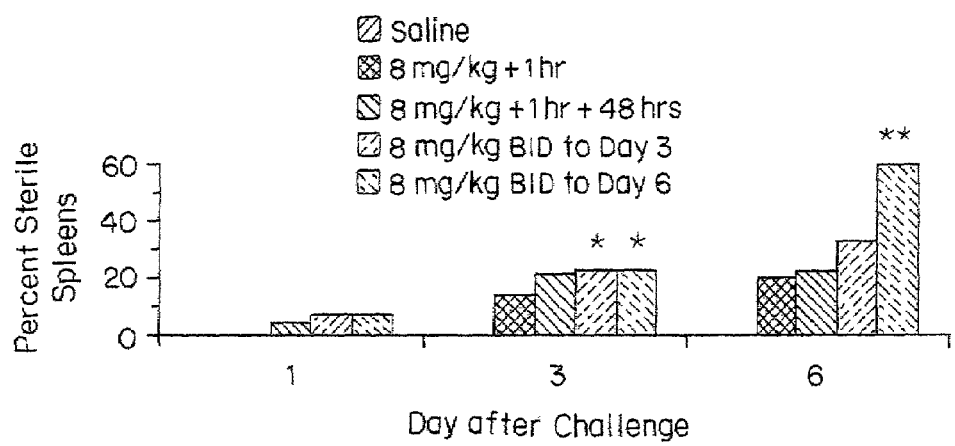
FIG. 8 is a bar graph illustrating the effect of VHMW-glucan on sterile spleen CFU levels in mice challenged with *E. coli* (multiple dosages).
Figure 9:
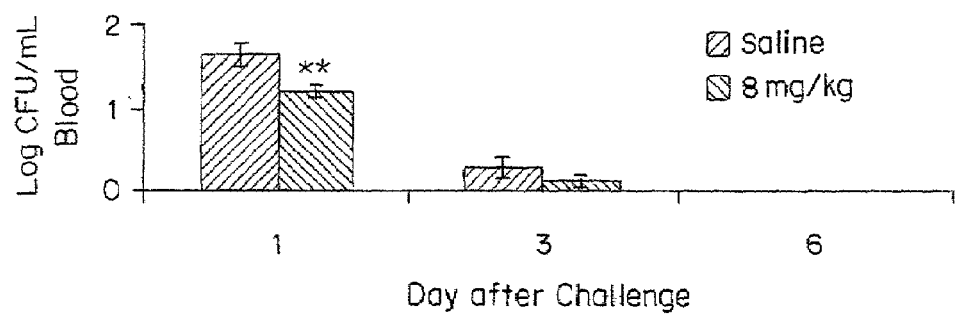
FIG. 9 is a bar graph illustrating the effect of VHMW-glucan on blood CFU levels in mice challenged with *E. coli*. VHMW-glucan was administered BID (twice daily) to day 3 after challenge.
Figure 10:
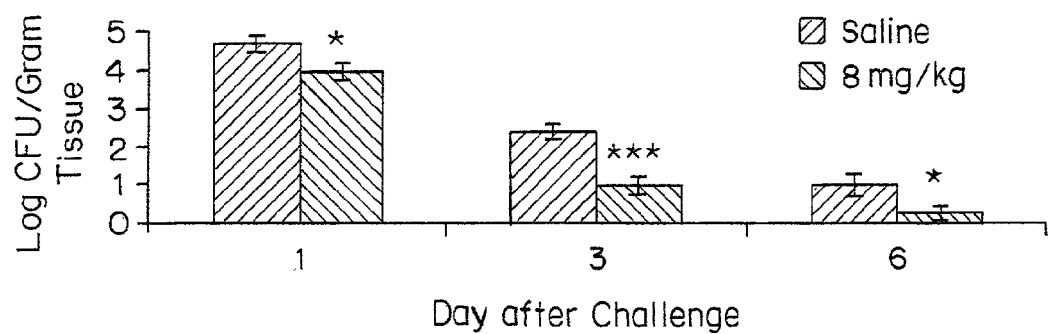
FIG. 10 is a bar graph illustrating the effect of VHMW-glucan on spleen CFU levels in mice challenged with *E. coli*. VHMW-glucan was administered BID to day 3 after challenge.
Figure 11:
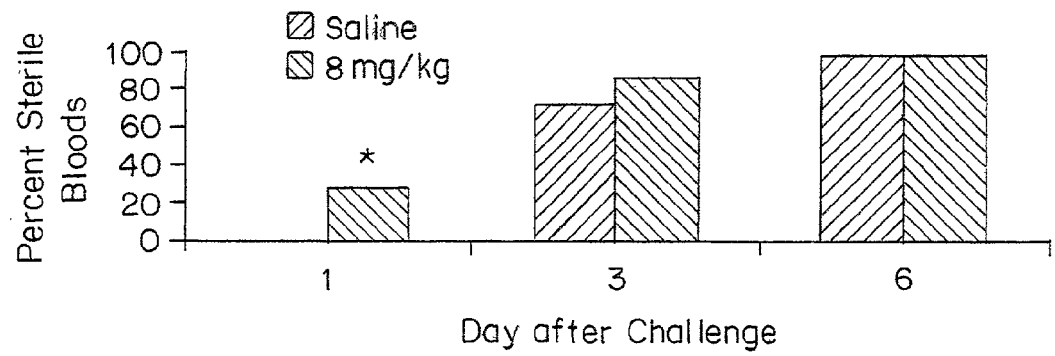
FIG. 11 is a bar graph illustrating the effect of VHMW-glucan on sterile blood CFU levels in mice challenged with *E. Coli*. VHMW-glucan was administered BID to day 3 after challenge.
Figure 12:
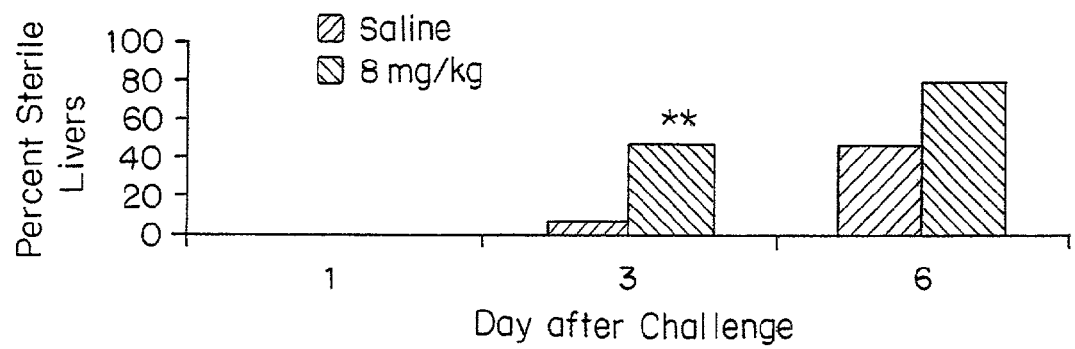
FIG. 12 is a bar graph illustrating the effect of VHMW-glucan on sterile liver CFU levels in mice challenged with *E. coli*. VHMW-glucan was administered BID to day 3 after challenge.

The results presented in FIG. 6 suggested that multiple doses of VHMW-glucan may be necessary to sustain CFU clearance at later days postchallenge. Hence, a series of studies were performed to compare the effects of 8 mg/kg of VHMW-glucan administered in multi-dose regimens. The first multi-dose regimen consisted of two VHMW-glucan treatments administered at +1 hr and +48 hr after challenge. Administration of the second VHMW-glucan dose at +48 hr sustained significantly enhanced CFU clearance through day 3, however, effects were again lost by day 6 after VHMW-glucan administration. The next experiment evaluated whether further increasing the frequency of VHMW-glucan treatment would further sustain or accelerate CFU clearance (FIG. 7). Compared to mice administered either one (+1 hr) or two (+1 hours and +48 hours) VHMW-glucan treatments, mice receiving VHMW-glucan at +1 hours and then every 12 hours to day 3 (6 treatments) or at +1 hours and then every 12 hours to day 6 (12 treatments) exhibited progressively enhanced splenic CFU clearance. Increasing the frequency of dosing also resulted in complete elimination of *E. coli* in a greater percentage of spleens (FIG. 8). Animals treated with the 8 mg/kg 6-treatment VHMW-glucan regimen were further evaluated for effects on CFU clearance in other tissues. Evaluation of CFU levels in the blood (FIG. 9), liver (FIG. 10) and peritoneal fluid (data not shown) revealed that VHMW-glucan treatment also significantly accelerated CFU clearance in these tissues. VHMW-glucan treatment also resulted in complete elimination of *E. coli* in a greater percent of these tissues than saline treatment (FIGS. 11 and 12).

Effect of VHMW-glucan Treatment on WBC Counts.

Figure 13:
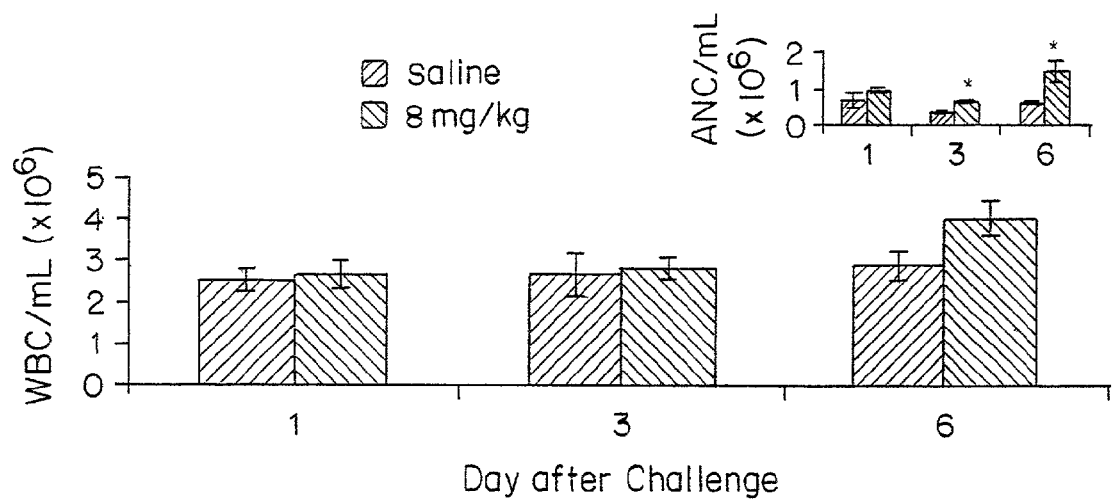
FIG. 13 is a bar graph illustrating the effect of VHMW-glucan on blood WBC levels in mice challenged with *E. coli*. VHMW-glucan was administered BID to day 3 after challenge. The insert is a bar graph illustrating the effect of VBMW-glucan on absolute neutrophil count (ANC/ml×$10^6$) in mice challenged with *E. coli*.

To evaluate whether the anti-infective activity of VHMW-glucan was related to an ability to increase WBC numbers, blood cell counts were performed on days 1, 3 and 6 following the 8 mg/kg 6-treatment VHMW-glucan regimen in mice challenged with *E. coli*. Following *E. coli* challenge, WBC count appeared to be increased in VHMW-glucan treated animals only at day 6 post challenge (FIG. 13). However, based on differential analysis, an increase in absolute neutrophil counts (ANC) occurred on both day 3 and day 6 (FIG. 13 insert).

Effect of VHMW-glucan Treatment on Leukocyte Oxidative Burst Activity.

To evaluate whether VHMW-glucan treatment altered leukocyte oxidative microbicidal activity, mice challenged with *E. coli* were injected with the 8 mg/kg 6-dose VHMW-glucan regimen and PEF and spleen leukocytes evaluated for oxidative burst activity on days 1, 3 and 6 after challenge. Elevated oxidative burst activity was seen on day 3 with PEF cells and on days 1, 3 and 6 with spleen leukocytes (data not shown).

Effect of VHMW-glucan on Cytokine Release.

Figure 14:
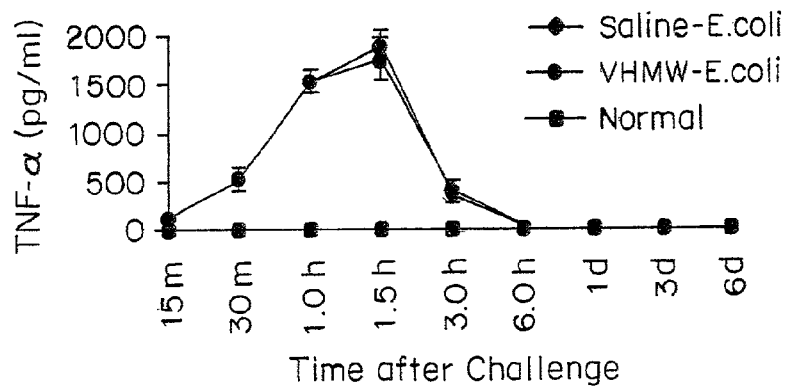
FIG. 14 is a graph illustrating the effect of VHMW-glucan therapy on serum TNF-α levels in mice challenged with *E. coli*. Saline-*E. coli* (diamond); VHMW-*E. coli* (circle); normal (box).
Figure 16:
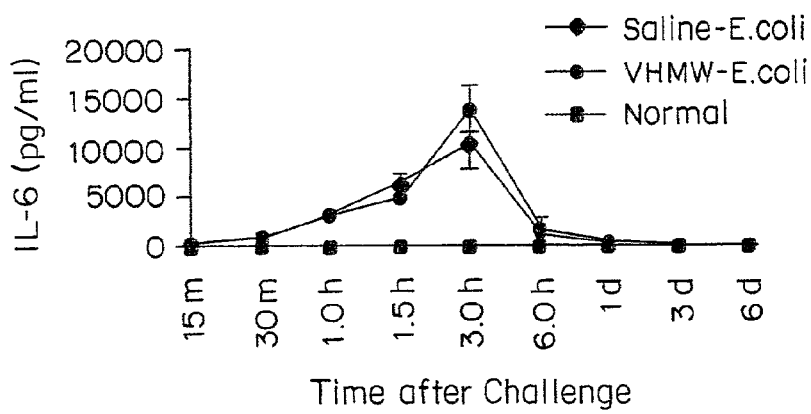
FIG. 16 is a graph illustrating the effect of VHMW-glucan therapy on serum IL-6 levels in mice challenged with *E. coli*. Saline-*E. coli* (diamond); VHMW-*E. coli* (circle); normal (box).

Proinflammatory cytokines have previously been shown to possess anti-infective activity (Holyoake, T. L., *Blood Rev.*, 10:189–200 (1996). The effects of the 8 mg/kg 6-dose VHMW-glucan regimen on cytokin induction in mice challenged with *E. coli* was examined. Although *E. coli* challenge induced cytokine production, VHMW-glucan treatment did not further elevate TNF-α, IL-1β or IL-6 levels in *E. coli* infected mice. See FIGS. 14 to 16.

While this invention has been particularly shown and described with references to preferred embodiments thereof, it will be understood by those skilled in the art that various changes in form and details may be made therein without departing from the spirit and scope of the invention as defined by the appended claims.

We claim:

1. A method for enhancing myclopoeisis and thrombopoeisis comprising administering to an animal or human the aqueous soluble underivatized, β-glucan composition comprising β-glucan molecules having an average molecular weight of at least 1,000,000 daltons, as determined by multi-angle laser light scattering, wherein the composition has a triple helix aggregate conformation and enhances immune response without inducing TNF-α, IL-1β and IL-6, in an amount sufficient for enhancing myelopoeisis and thrombopoeisis.

2. An aqueous soluble β-glucan composition comprising β-glucan molecules having a molecular weight of about 2,000,000 daltons to about 4,000,000 daltons as determined by a multi-angle laser light scattering, wherein the composition has a triple helix aggregate conformation and enhances immune response without stimulating production of biochemical mediators that induce detrimental side effects.

3. A method of inducing an immune response in an animal or human comprising administering to the animal or human the aqueous soluble underivatized, β-glucan composition of claim 2, in an amount sufficient for inducing an immune response.

4. A method for treating infection in an animal or human, comprising administering to the animal or human the aqueous soluble underivatized, β-glucan composition of claim 2, in an amount sufficient to treat infection.

5. A method for stimulating repair and healing of a wound site on an animal or human comprising administering to the wound site the aqueous soluble underivatized, β-glucan composition of claim 2, in an amount sufficient for stimulating repair and healing of a wound site.

6. A method for stimulating wound healing and treating infections associated with the wound, comprising administering to the wound site the aqueous soluble underivatized β-glucan composition of claim 2, in an amount sufficient for stimulating wound healing and treatment of wound infection.

7. A method for enhancing the microbicidal activity of phagocytic cells comprising administering to a animal or human the aqueous soluble underivatized, β-glucan composition of claim 2, in an amount sufficient for enhancing the microbicidal activity of phagocytic cells.

8. A method for stimulating hematopoiesis comprising administering to an animal or human the aqueous soluble underivatized, β-glucan composition of claim 2, in an amount sufficient for stimulating hematopoiesis.

9. A method for treating refractory infections comprising administering to an animal or human the aqueous soluble underivatized, β-glucan composition of claim 2, in an amount sufficient for treating refractory infections.

10. A method for stimulating the production of platelet in an animal or human, comprising administering to the animal or human the aqueous soluble underivatized, β-glucan composition of claim 2, in an amount sufficient for stimulating the production of platelet.

11. A method for therapeutically treating an animal or human having an established infection, comprising administering to the animal or human the aqueous soluble underivatized β-glucan compositions of claim 2, in an amount sufficient for treating the infection.

12. A method of accelerating bacterial clearance in an animal or human having an established infection comprising administering to the animal or human the aqueous soluble underivatized β-glucan compositions of claim 2, in an amount sufficient for accelerating bacterial clearance.

* * * * *